(12) United States Patent
Porta et al.

(10) Patent No.: US 6,767,554 B2
(45) Date of Patent: Jul. 27, 2004

(54) USE OF COMPLEXES AMONG CATIONIC LIPOSOMES AND POLYDEOXYRIBONUCLEOTIDES AND MEDICAMENTS

(75) Inventors: Roberto Porta, Como (IT); Laura Ferro, Milan (IT); Fabio Trento, Como (IT); Claudio Nastruzzi, Ferrara (IT); Elisabetta Esposito, Ferrara (IT); Enea Menegatti, Ferrara (IT)

(73) Assignee: Gentum S.p.A., Como (IT)

( * ) Notice: Subject to any disclaimer, the term of this patent is extended or adjusted under 35 U.S.C. 154(b) by 0 days.

(21) Appl. No.: 09/330,215

(22) Filed: Jun. 11, 1999

(65) Prior Publication Data

US 2002/0142029 A1 Oct. 3, 2002

(51) Int. Cl.$^7$ ............................................... A61K 9/127
(52) U.S. Cl. ......................................... 424/450; 514/44
(58) Field of Search ........................... 424/450; 514/44, 514/822, 886; 935/54

(56) References Cited

U.S. PATENT DOCUMENTS

| | | | | |
|---|---|---|---|---|
| 3,770,720 A | 11/1973 | Butti et al. | ............... | 260/211.5 |
| 4,985,552 A | 1/1991 | Fedeli et al. | ................... | 536/27 |
| 5,908,777 A | * 6/1999 | Lee et al. | | |

FOREIGN PATENT DOCUMENTS

| | | |
|---|---|---|
| EP | 039471 | 11/1981 |
| EP | 539989 | 5/1993 |
| EP | 0 558833 A | 9/1993 |
| EP | 562509 | 9/1993 |
| EP | 634384 | 1/1995 |
| WO | 90 10448 A8 | 9/1990 |
| WO | 96 18372 A | 6/1996 |
| WO | WO 97/04787 | 2/1997 |
| WO | 97 04787 A | 2/1997 |

OTHER PUBLICATIONS

Eastman in Human Gene Therapy 8, p 765, 1997.*
Maccarone 186 #3, BBRC p 1417, 1992.*
Petra Lobel and Karsten Schror, A therosclerosis, 80; Elsevier Scientiric Publishers Ireland, Ltd., "Stimulation of Vascular Prostacyclin and Inhibition of Platelet Function by Oral Defibrotide in Cholesterol–Fed Rabbits", pp. 69–79 (1989).
Katsuhiko Miyasaka and Takashi Mikami, European Journal Pharmacology, 77; Elsevier/North–Holland Biomedical Press, "Comparison of the Anti–Inflammatory Effects of Dexamethasone, Idomethacin and BW755C on Carrageenin–Induced Pleurisy in Rats", pp. 229–236 (1982).
Francis Szoka, Jr. and Demetrios Papahadjopoulos, Proc. Natl. Acad. Sci. USA, vol. 75, No. 9, "Procedure for Preparation of Liposomes with Large Internal Aqueous Space and High Capture by Reverse–Phase Evaporation", pp. 4194–4198.

David C. Litzinger et al., Biochimica et Biophysica Acta, 1281, "Fate of Cationic Liposomes and Their Complex with Oligonucleotide in Vivo", pp. 139–149 (1996).
R.R.C. New, IRL Press, "Liposomes, a Practical Approach", pp. 51–54 (1994).
Rollin D. Hotchkiss, Nucleic Acids and Derivatives, "Methods for Characterization of Nucleic Acid", [105 ] pp. 708–712.
Christoph Thiemermann, BSc, et al., The American Journal of Cardiology, "Usefulness of Defibrotide in Protecting Ischemic Myocardium from Early Reperfusion Damage", pp. 978–982 (1985).
Rosario Scalia, et al., Meth Find Exp. Clin Pharmacol, "Effects of Defibortide on Leukocyte–Endothelial Cell Interaction in the Rat Mesenteric Vascular Bed: Role of P–Selectin", 18(10), pp. 669–676 (1996).
Giuseppe Rossoni et al., Journal of Cardiovascular Pharmacology™,"Vasoconstriction to Polymorphonuclear Leukocytes in the Isolated, Perfused Rabbit Heart: Inhibition by Prostacyclin Memetics", 27, pp. 680–685 (1996).
F. Trento, et al., Centro Congressi Unione Industriale, "Interaction of the Endothelial Mediators, No and PGI$_2$, on the Regulation of Blood Pressure in Anaesthetized Rats", XXVII Congresso Nazionale Della Scoieta Italiana Di Farmacologia, Abstracts, Torino, pp. 25–29 (Sep. 1994).
R. Niada et al., Pharmacological Research Communications, The Italian Pharmacological Society, "PGI$_2$–Generation and Antithrombotic Activity of Orally Administered Defibrotide", pp. 949–957 (1982).
R. Pescador et al., Thrombosis Research, "Pharmacokinetics of Defibrotide* and of Its Profibrionlytic Activity in the Rabbit", 30, pp. 1–11 (1983).
Alain Colige et al., Biochemistry, "Use of an Antisense Oligonucleotide to Inhibit Expression of a Mutated Human Porcollagen Gene (COLIA1) IN Transfected Mouse 3T3 Cells", 32, pp. 7–11 (1993).
A. Gursoy et al., Pharmazie, "Preparation, Characterization and Anti–Inflammatory Effect of Defibrotide Liposomes", 48, H., pp. 549–550 (1993).
Xiang Gao and Leaf Huang, Biochemical and Biophysical Research Communications, "A Novel Cationic Liposome Reagent for Efficient Transfection of Mammalian Cells", vol. 179, No. 1, pp. 280–285 (1991).
C. Frank Bennett et al., The American Society for Pharmacology and Experimental Therapeutics, Cationic Lipids Enhance ICAM–1 Antisense Oligonucleotides, "Cationic Lipids Enhance Cellular Uptake and Activity of Phosphorothioate Antisense Oligonucleotides", pp. 1023–1033 (1992).

(List continued on next page.)

Primary Examiner—Gollamudi S. Kishore
(74) Attorney, Agent, or Firm—Arent Fox, PLLC

(57) ABSTRACT

The invention relates to the use as medicaments, specifically as antiinflammatories, of complexes formed by cationic liposomes and polydeoxyribonucleotides having a molecular weight in the range 7,000–60,000 Da obtainable by depolymerization of nucleic acids, wherein in said complexes the polydeoxyribonucletoides are located on the outer surface of the liposome.

15 Claims, No Drawings

OTHER PUBLICATIONS

Geneve, *Informations Pharmaceutiques*, vol. 1, No. 4, Listes Recommandees DCI 27, Denominatios communes Internationales Des Substances Pharmaceutiques, Organisation Mondiale de la Sante—Geneve, p. 272 (1987).

Zelphati et al. "Cationic Liposomes as an Oligonucleotide Carrier: Mechanism of Action" *Journal of Liposome Research, U.S.*, Marcel Dekker, NY, Jan. 1, 1997, vol. 7, No. 1, pp. 31–49.

* cited by examiner

USE OF COMPLEXES AMONG CATIONIC LIPOSOMES AND POLYDEOXYRIBONUCLEOTIDES AND MEDICAMENTS

The present invention relates to the use as medicaments of complexes formed by cationic liposomes and polydeoxyribonucleotides. More specifically the present invention relates to the use of the above mentioned complexes which possess a remarkable stability in time as medicaments having anti-inflammatory activity.

It is well known that the liposomes can be used as carriers for drug systemic administration. They are administered by intravenous, subcutaneous, intramuscular injection, or by infusion.

As far as the structure of the complexes between liposomes and DNAS is concerned, it is known that oligodeoxyribonucleotides and plasmid DNAs can bind by means of an ionic bond to the external surface of cationic liposomes (C. F. Bennet et Al. Mol. Pharmacol. 41,1023–1033,1992; Xiang Gao et Al. Biochem. Biophys. Res. Comm. 179, 280–285, 1991). However no indication is given on the stability in the time of said complexes and on their use as anti-inflammatory drugs. It is also known by the patent application WO 97/04787 that when oligonucleotides have a chain length between 8 and 50 nucleotides, they can be entrapped into liposomes. Also in this reference no information is given on the stability of the complexes in the time.

Complexes with liposomes and polydeoxyribonucleotides having molecular weight of 16000 Da, obtained by depolymerization of nucleic acids, wherein these polymers are contained inside the lipidic vesicle (Gursoy et Alii, Pharmazie 48, (1993)H. 7, 559–560 ), have been described. The same as above said for WO 97/04787 can be repeated.

It is also known that liposome complexes with oligonucleotides and polydeoxyribonucleotides have the property to remarkably increase the pharmacologic activities of the latter substances (Bennet et Al, Gursoy et Al., see above; A. Colige, Biochemistry 1993, 32, 7–11). However tests carried out by the Applicant have shown that these complexes of the prior art cannot be used as therapeutical agents because, when suspended in aqueous media as requested for their administration, they loose very quickly their activity in time. Besides this, in said complexes the cationic components of the liposome, such as for example stearylamine and quaternary ammonium surfactants, can be potentially toxic agents and can cause toxic side effects. The complex degradation is also evident since the physical appearance of the aqueous phase changes in time, turning from opalescent (initial emulsion) to final limpid, with formation of a precipitate.

The polydeoxyribonucleotides, and specifically that know as defibrotide, are well known as medicaments having profibrinolytic activity (R. Pescador et al., Thromb. Res. 30: 1–11, 1983), antithrombotic-thrombolytic (R. Niada et Al., Pharmacol. Res. Commun. 14 (10), 949–957 1982) antihypertensive (F. Trento et Al., XXVII Congr. Naz. Soc. It. Farmacol. Torino 25–29 September 1994, Abstract Book pag. 703), antiischaemic, cytoprotective (G. Rossoni et Al. J. Cardiovasc. Pharmacol. 27, 680–685 1986) and anti-inflammatory activity (R. Scalia, Meth. Find. Exp. Clin. Pharmacol. 18(10) 669–676 1996). The daily doses range from 600 to 1200 mg. All these pharmacologic activities of the substance are essentially referable to their property to locally release therapeutically effective amounts of endogenous prostacyline from the vascular endothelium (ref. R. Niada et alii, above, C. Thiemermann et Alii, Am. J. Cardiol. 56 978–982 1985).

It has been now surprisingly and unexpectedly found by the Applicant that it is possible to prepare complexes from liposomes and polydeoxyribonucleotides having an high activity lasting in time, devoid of any toxic side effect.

This affords to use the aqueous emulsions containing the complexes of the invention for subsequent treatments, for one or more days, and also also for long lasting administrations, such as infusions.

Therefore it is an object of the invention the use as medicaments, specifically as anti-inflammatories, of complexes formed by cationic liposomes and by polydeoxyribonucleotides having a molecular weight in the range 7,000–60,000, preferably 10,000–60,000, most preferably 15,000–60,000 Da, obtainable by depolymerization of nucleic acids, wherein the polydeoxyribonucleotides are located on the outer surface of the liposome.

Said liposome complexes are characterized in that their solutions, by addition of aliquots of at ceytlpyridinium chloride solution, form a quantity of a precipitate with said quaternary ammonium ion that is different from that obtainable by treating in the same conditions a solution of the liposome complexes of the same polydeoxyribonucleotides and cationic liposomes wherein the polydeoxyribonucleotides are instead located inside the liposome.

In a preferred embodiment of the invention the polydeoxyribonucleotide is defibrotide.

Therefore according to the present invention it is also possible to reduce the daily dose to be administered to the patient, without affecting the therapy effectiveness.

The liposomes are lipidic vesicles, which are formed in aqueous phase, and are generally constituted of phospholipides. Said compounds in the presence of water and an insoluble organic solvent form a spherical shell which wall is a double layer, wherein the molecule polar portion (hydrophilic) is on the outer side of the liposome and the lipidic portion (hydrophobic) is inside the double layer. The vesicle in this case is called monolamellar. There are also multilamellar liposomes, which are composed of more lipidic layers.

The polydeoxyribonucleotides having a molecular weight in the range 15,000–60,000 which are used in the complexes with liposomes according to the present invention are obtainable by extraction and subsequent depolymerization of high molecular weight nucleic acids.

The extraction of high molecular weight nucleic acids can be carried out as disclosed in the U.S. Pat. No. 3,770, 720, herein incorporated by reference. It is possible to obtain polydeoxyribonucleotides with molecular weight in the range 15,000–30,000 by carrying out the depolymerization of nucleic acids as described in U.S. Pat. No. 4,985,552 herein incorporated by reference. The Applicant has ascertained that it is possible to obtain also polymers having a molecular weight in the range 30,000–60,000, using the same conditions of the process of U.S. Pat. No. 4,985,552 stopping depolymerization when the value of reversible hyperchromicity, as defined in Methods in Enzymol. vol. III pag. 708–712, is comprised between 20 and 40% (with reference to the absorbance value of reversible hyperchromicity the non denatured sample), or, stopping depolymerization when the value of reversible hyperchromicity is above or equal to 3 for obtaining polydeoxyribcnucleotides having molecular weight above or equal to 7,000. Reversible hyperchromicity is the parameter by which depolymerization progress is followed, The preferred polydeoxyribonucleotides to form the complex with the cationic liposome are the ones known as defibrotides (D.C.I.) having a molecular weight in the range 15,000–30,000 (Informations Pharmaceutiques O.M.S. n. 4, vol. 1/1987 pag. 272).

The main lipidic components of the liposomes of the invention are phosphatidylcoline or phosphatidylethanolamine, which can be combined in the liposome with other lipids as disclosed in the R.R.C. New volume "Liposomes, a practical approach" IRL Press 1994, herein incorporated by reference. The preferred associated lipids are ergosterol and cholesterol.

One or more antioxidants, selected from the known ones and which are listed in the same reference previously mentioned, can be added to the composition. The preferred antioxidant is alpha-tocopherol.

To the liposomes of the invention are added cationic surfactants, containing one or more mono-, di-substituted amminic groups, or quaternary ammonium groups. Said quaternary ammonium groups contain one or more aliphatic chains with a number of carbon atoms ranging from 8 to 22.

The quaternary ammonium surfactants having aliphatic chains with 18 carbon atoms, are preferred.

The molar ratio between the total amount of the liposome lipid/s and cationic surfactant ranges from 10:0.05 to 10:3, preferably is 10:1. When together with the phosphatidylcoline (or phosphatidylethanolamine) there is a second and different lipid, the internal molar ratios between each of the two lipids and the surfactant (phosphatidylcoline (or phosphatidylethanolamine): second lipid: surfactant) range from 9:1:0.05 to 7:3:3, preferably 8:2:1.

The weight ratio between the liposome amount and that of the active principle (polydeoxyribonucleotides) ranges from 10:2 to 10:0,1, preferably is 10:1.

The preparation of the cationic liposome complexes used in the present invention can be carried out as described by D. C. Litzinger, Biochim. Biophys. Acta 1281 139–149, 1996, or in the above mentioned R. R. C. New's volume. In particular a process usable for preparing the present invention complex comprises the following steps:

a. liposome preparation by means of the solvent reverse phase evaporation method, ref. Szoka P. et Alii. Proc. Natl. Acad. Sci. USA 75 4194 1978): 4 parts of organic phase, which can be polar (ex. linear or branched $C_1$–$C_4$ lower aliphatic alcohols) or apolar (ex. linear or branched $C_1$–$C_4$ dialkylethers, such as for example diethylether, partially chlorinated $C_1$–$C_2$ hydrocarbons, preferably chloroform), wherein are solubilized the lipids, the cationic surfactant and the antioxidant, with one part of water, the thus obtained biphasic system is subjected to sonication at 0° C. for 5–20 minutes, the organic phase is then evaporated at room temperature at a reduced pressure, thus obtaining an emulsion, flowing said emulsion, according to the technique described at pages 52–54 of the R. R. C. New volume, through a polycarbonate membrane having a pore diameter ranging from 100 to 600 nm, preferably 400 nm; the step is repeated for at least three times, so to obtain a vesicle average diameter comparable with that of the membrane pores, lyophilizing the aqueous emulsion, after addition of an aqueous solution of a lyophilizing coadjuvant, for example monosaccharides such as saccharose, sorbitol, mannitol, fructose, or polysaccharides such as dextranes, maltodextrines having different molecular weight, so that the coadjuvant is in excess of at least 7 times with respect to the lipids. Preferably the excess is comprised between 10 and 15 times, preparation of the final emulsion for pharmaceutical use by adding in a sterile environment, under stirring, a diluted sterile isotonic aqueous solution of polydeoxyribonucleotides to the vessel containing the lyophilized emulsion. An emulsion is formed containing a liposome complex wherein the polydeoxyribonucleotides are linked with an ionic bond to the liposome outer wall. Alternatively, a sterile isotonic solution is added to the vessel containing the lyophilized liposomes and the so obtained emulsion is mixed in a sterile environment with the solution containing the active principle.

The stability of the liposomes of the invention has been evaluated by assaying the pharmacologic activity immediately after the emulsion preparation and then at the 30th day of conditioning under sterile conditions at 25° C. in the dark.

The emulsion containing the entrapped polydeoxyribonucleotides liposome complex (Gursoy et al, see above) underwent the same test and was used as comparative formulation.

The Applicant has also found that the present invention complexes can be used also as antihypertensive and antithrombotic agents having an high activity in the time, without side toxic effects.

The pharmacologic activity has been determined in the following experimental models.

Anti-inflammatory activity (Miyasaka et al., Eur. J. Pharmacol. 77 229–236 1982).

Arterial hypertension (F. Trento et Al., see above).

Antithrombotic activity (R. Niada et alii, Thromb. Res. 23 233–246. 1981).

In the experiment relating to the anti-inflammatory activity the myeloperoxidase amount present in the obtained polymorphonucleates of the animal pleural exudate, has been assayed. The enzyme amount is directly proportional to the produced inflammation. The results are expressed as % variation of the myeloperoxidase (MPO) amount with respect to that of the controls, determined with the formula:

$$\frac{MPO_{Treated} - MPO_{Controls}}{MPO_{Controls}}$$

In the arterial hypertension model the parameter used to determine the activity was blood-pressure which was monitored up to 30 minutes from the treatment with L-NAME, the inhibitor of the release of endogenous nitric oxide. In the antithrombotic activity model the carotid temperature has ben monitored up to 60 minutes after induction of the local endothelial lesion. The results have been expressed as % variation of the area under the curve ($\Delta AUC$ %) obtained with the tested sample with respect to that of the controls, by means of the following ratio:

$$\frac{Area_{Treated} - Area_{Controls}}{Area_{Controls}}$$

The obtained results, reported respectively in Tables I, II and III, show that the complex among liposomes and polydeoxyribonucleotides according to the present invention is stable in time, differently from the comparative formulation.

According to the present invention it is therefore possible to administer to the patient a lower amount of active principle maintaining the therapeutic effect unchanged.

It is also possible to use a same complex emulsion, suitably formulated and with a suitable active principle concentration, for a whole therapy cycle as requested in the above mentioned pathologies.

It is also known that polydeoxyribonucleotides known as defibrotide have an antithrombotic activity (R. Niada, Pharmacol. res. Comm., see above), anti-ischaemic, cytoprotective (C. Thiermemann, see above), anti-inflammatory activity (G. Rossoni, J. Cardiovasc. Pharmacol., see above) and in the atherosclerosis (P. Lobel et Al. Atherosclerosis 80, 69–79 1989). Said actitivites are referable to the local release of endothelial prostacyclin in the blood flood in therapeutically effective amounts.

It has been found by the Applicant that the liposome-polydeoxyribonucleotide complexes described in the present invention can be used for the therapy of pathologies which treatment requires a sustained release of endothelial prostacyclin.

The pharmaceutical formulations containing the cationic liposome-polydeoxyribonucleotides include the usual carriers and excipients. Said formulations can be in the form of sterile and apyrogenic emulsions, or of lyophilisates, stored in sterile containers, to be extemporaneously dissolved in sterile aqueous solvents. In the latter case it is preferred that the liposome lyophilisate is separately stored and that the polydeoxyribonucleotides are already dissolved in the aqueous sterile solvent to be added to the liposomes.

As aqueous sterile solvents, sterile isotonic solutions containing conventional buffers (citrates, phosphates) can be used together with known preservatives.

The administration routes of the emulsion containing the complex of the invention are those parenteral, i.e. by intravenous, intramuscular, subcutaneous injection, and by infusion.

The active principle amount contained in the preparation ranges from 1 to 20 mg/ml of polydeoxyribonucleotide.

The polydeoxyribonucleotide daily doses administered with the liposome complexes range from 10 to 200 mg, preferably from 20 to 120 mg.

The following examples have the purpose to clarify the content of the present invention and are not to be considered as a limitation of the scope of the same.

EXAMPLE 1

Preparation of the polydeoxyribonucleotide liposomes.

The preparation of the liposomes used in the present invention is carried out according to the solvent reverse phase evaporation method.

100 mg of soya phosphatidylcoline (Phospholipon® 90-Natterman Phospholipid GmbH), dioctadecyldimethyl ammonium bromide (abbr. DIDAB-Fluka Chemie AG) and 0.1% w/w of alphatocopherol (Fluka Chemie AG) are dissolved in diethylether. Phosphatidylcoline and cationic surfactant are mixed in a 10:1 molar ratio.

To the organic phase, bidistilled water is added in a ratio of 4 parts of organic phase/1 part of water, thus obtaining an emulsion W/O.

On the emulsion a sonication at 0° C. is carried out for 10 minutes by using a Branson 2200 sonicator batch. The ether is then removed by evaporation at a reduced pressure until an aqueous liposomal system is obtained, which is then made to flow through polycarbonate membranes (Nucleopore) having a pore diameter of 0.4 $\mu$m. Said step through the membrane is repeated three more times A mannitol amount equal to 10 times the lipid weight is added and the suspension is lyophilized.

50 mg of a polydeoxyribonucleotide having a molecular weight of 28,000, obtained by depolymerization according to U.S. Pat. No. 4,985,552, are dissolved in 5 ml of isotonic physiologic solution. The above obtained lyophilizate is dissolved in 5 ml of bidistilled water. The two aqueous phases are mixed and stirred. In the so obtained emulsion the concentration of phosphatidylcoline is of 10 mg/ml and that of the polydeoxyribonucleotide is of 5 mg/ml.

EXAMPLE 2

Comparative

Preparation of polydeoxyribonucleotide liposomes according to the prior art (Gursoy et alii, Pharmazie 48 (19–93) H 7 559–560) having the polydeoxyribonucleotide entrapped in the liposome.

The same organic phase of Example 1, with the same components mentioned above, is separately dried in a vessel. An aqueous solution of a polydeoxyribonucleotide having molecular weight 16,000, prepared as the polydeoxyribonucleotide solution of the previous example is added. The liposomal vesicles englobing the active principle are obtained by sonication. The phosphatidylcoline and polydeoxyribonucleotide concentrations are the same as those in the complex of example 1.

EXAMPLE 3

Demonstration of the formation of the polydeoxyribonucleotide-liposome complex of Example 1 by electrophoretic method.

The electrophoresis is carried out in a 3% agarose gel containing 0.5 $\mu$g/ml of ethidium bromide as fluorescence agent. The electrophoretic system is constituted by a small electrophoretic chamber containing a layer of gel of thickness comprised between 1–3 mm, to which a 50 mV electric field is applied.

In the gel are respectively seeded, in 6 separate zones near the negative pole, 20 $\mu$l of the solution of Example 1 (polydeoxyribonucleotide concentration 5 mg/ml), and of solutions containing the polydeoxyribonucleotide alone at concentrations of 4, 3, 2, 1, 0.5 mg/ml.

The electric field is applied for 40 minutes. The polydeoxyribonucleotide moves from the seeding zone towards the positive pole. At the end of the electrophoretic run the agarose gel is stained with ethidium bromide. The liposome complex does not show any coloration. In the gel are evidenced the bands corresponding to the seeds of the polydeoxyribonucleotide solutions, which intensity is proportional to the amount seeded.

EXAMPLE 4

Comparison of the stability of the liposome-polydeoxyribonucleotide complex obtained according to Example 1 with that of the complex wherein the polydeoxyribonucleotide is contained inside the liposome (Example 2 comparative), by evaluating the polydeoxyribonucleotide anti-inflammatory activity in rats treated with samples of solutions of said complexes freshly prepared and with samples of said solutions conditioned for 30 days at 25° C. in closed vessels, in the dark.

Sprague Dawley male rats weighing 250–270 g were used.

3 groups, each group of 18 animals, were formed and to each of the groups were respectively administered intravenously one of the following solutions at the stated doses:

1. Control group: physiologic solution, at 2 ml/Kg.
2. Group treated with the liposome-polydeoxyribonucleotide complex (ref. Ex. 1): physiologic solution containing the complex in amounts equal to a polydeoxyribonucleotide concentration of 1 mg/ml, at 2 mg/Kg.
3. Group treated with the liposome-polydeoxyribonucleotide complex according to A. Gursoy et alii (see above): physiologic solution containing the complex in amounts equal to a polydeoxyribonucleotide concentration of 1 mg/ml, at a 2 mg/Kg dose.

30 minutes after the treatment, under a mild ether anaesthesia, pleuritis was caused in the animals by administering by intrapleural route 0.5 ml of a 1% w/v carragenine physiologic solution and of 5 ml of water per os.

After 6 hours the animals were sacrificed. By means of a syringe the pleural exudate was recovered, and the content in polymorphonucleate neutrophil leucocytes (PMN) was determined by asssaying the myeloperoxidase (MPO) enzyme, which is the characteristic enzyme of these cells.

The assay was carried out as described-Schierwagen C. et Al. J. Pharmacol. Methods 23 179 1990.

The exudate samples were stirred and then 0.2 ml were added to 4.8 ml of a 0.5% w/v HTAB (hexadecyltrimethylammonium bromide) buffered solution. The samples were then frozen at −80° C. so as to cause cell breaking, unfrozen and then subjected to 80 watt sonication for 1 minute. The preparations were then heated to 60° C. for two hours in order to degrade the myeloperoxidase inhibitors and subsequently centrifuged at 11,800 g for 5 minutes at 4° C.

Before proceeding to the enzyme spectrophotometric assay (wavelength 650 nm), the samples were diluted with the HTAB solution in order to bring the reading values in the range of the standard curve obtained by using the pure MPO enzyme.

The results are expressed as per cent variation with respect to the MPO amount found in the controls and are reported in the following Table I.

The Table evidences that the anti-inflammatory activity of the two preparations at time zero is substantially the same and after 30 days the activity of the preparation according to the invention does not significantly differ from the initial value, while the preparation containing the liposomes according to the comparative example shows a 70% activity decrease with respect to the initial value. At the same time it was noticed that said latter preparation was degraded, since the aqueous phase appeared limpid and a precipitate was present that could not be resuspended.

The animals treated with this preparation showed evident signs of pain and pronounced dyspnoea.

EXAMPLE 5

Comparison of the stability of the liposome-polydeoxyribonucleotide complex obtained according to Example 1 with that of the complex wherein the polydeoxyribonucleotide is contained inside the liposome (Example 2 comparative), by evaluating the polydeoxyribonucleotide anti-hypertensive activity in rats, with hypertension induced by inhibition of endogenous nitric oxide (NO) release, administered with the samples of solutions containing the above complexes freshly prepared and with samples of the same solutions conditioned at 25° C. for 30 days in closed vessels in the dark.

Sprague Dawley male rats weighing 250±20 g, not fasted are anaesthetized with ethylurethane. Two catheters were respectively inserted in the left carotid artery, for recording the mean arterial blood pressure (MABP), and in the right jugular vein, for administering the tested compositions. The trachea was cannulated and the animal body temperature was maintained at 37° C. The MABP was continuously recorded throughout the experiment. Heparin (500 U.I./Kg i.v.) was administered to avoid blood coagulation in the recording system.

After 30 minutes the rats were randomized in homogeneous groups.

The treatment with the compositions or the placebo was carried out by bolus, immediately followed by perfusion. After one hour from the start of the perfusion all the animals receive an intravenous bolus of L-NAME (10 mg/Kg). The perfusion lasted 30 minutes after the injection of L-NAME.

The pressure modifications induced by the compositions are expressed as area under the curve (AUC) in the 30 minutes interval following L-NAME treatment.

In the experimental model under consideration the animals were divided in four groups (6 animals for group), each of them was intravenously treated with a bolus of 1 ml/Kg, immediately followed by a a perfusion of 2 ml/Kg/h, as explained hereinafter:

1. Control group (CTR): physiologic solution 1 ml/Kg bolus+2 ml/Kg/hour in perfusion.
2. Group treated with a bolus of a polydeoxyribonucleotide mol. wt. 28,000 in a physiologic solution at concentration of 10 mg/ml, at the dose of 10 mg/Kg (bolus)+20 mg/Kg/h in perfusion.
3. Group treated with a bolus of the liposome-polydeoxyribonucleotide complex of the invention in a physiologic solution at a polydeoxyribonucleotide concentration of 5 mg/ml, at the dose of 5 mg/Kg (bolus)+10 mg/Kg/h in perfusion.
4. Group treated with a bolus of the liposome-polydeoxyribonucleotide complex according the comparative example 2 in a physiologic solution at a polydeoxyribo nucleotide concentration of 5 mg/ml, at the dose of 5 mg/Kg (bolus)+10 mg/Kg/h in perfusion.

The pharmacologic activity determined by using samples of freshly prepared solutions containing the liposome complexes above referred, and samples of the same solutions stored in closed vessels at 25° C. in the dark, is reported in Table II.

The results show that whereas at time zero the two preparations have nearly the same antihypertensive activity, after 30 days the activity of the preparation according to the prior art is lowered of about 70% in the confront with the corresponding starting value.

The animals treated with said preparation showed evident signs of pain with marked dyspnoea.

EXAMPLE 6

Comparison of the stability of the liposome-polydeoxyribonucleotide complex obtained according to Example 1 with that of the complex wherein the polydeoxyribonucleotide is contained inside the liposome (Example 2 comparative), by evaluating the polydeoxyribonucleotide anti-thrombotic activity in rats, treated with samples of solutions containing the above complexes freshly prepared and with samples of the same solutions conditioned at 25° C. for 30 days in closed vessels in the dark.

Sprague Dawley male rats weighing 200–230 g, fasted for 16 hours, were anaesthetized with urethane (1.25 g/Kg i.p.).

After the right carotid artery and the left jugular vein of the animals were isolated. A bipolar electrode (Lesion Producing Device 3500 Ugo Basile—Comerio, Varese) was positioned on the right artery and, at a 0.5 cm distance, a thermosensitive probe connected to a polygraph. A catheter was inserted in the vein for administering the preparations.

After 15 minutes of stabilization, the carotid temperature was continuously recorded from 5 minutes before to 60 minutes after the endothelial lesion induction by means of the electrode. This allowed to indirectly determine the formation of endoluminal thrombi formation by correlation between the decreasing temperature of the vessel and the blood flow reduction. The endothelial lesion was caused by a series of 5 electric stimuli. The stimuli at intervals of one minute one from the other, were such that the impedance measured on the lesioned artery was of 10 mA. The impedance was measured with a tester and was regulated for each animal during the first 30 seconds of stimulation, and required applied voltage of about 30 Volt.

The carotid temperature was determined immediately before the electric stimulation (basal value) and at constant intervals of time (5, 10, 15, 30, 45 and 60 minutes) after the stimulation.

The groups were each formed by 10–12 rats.

All the treatments were carried out as intravenous bolus which was administered 5 minutes before the beginning of the electric stimulation.

The groups were the following:
1. Control group SHAM, wherein the animals were operated and monitored as above described, but they were not subjected to the electric stimulation.
2. Control group, treated with physiologic solution (1.5 ml/Kg i.v.).
3. Group treated with the liposome-polydeoxyribonucleotide complex (ref. Ex. 1): physiologic solution containing the complex in an amount equal to a polydeoxyribonucleotide concentration of 5 mg/ml; administered dose: 7.5 mg/Kg.
4. Group treated with the liposome-polydeoxyribonucleotide complex according to A. Gursoy et alii (see above): physiologic solution containing the complex in amounts equal to a polydeoxyribonucleotide concentration of 5 mg/ml; administered dose: 7.5 mg/Kg.

The activity was determined at the time of the preparation of the solutions with the two complexes and after 30 days of conditioning said solutions at 25° C. in the dark.

The results are reported in Table III.

From the Table it is noticed that while the antithrombotic activity of the two preparations at time zero is substantially comparable, after 30 days the activity of the preparation according to the prior art is lowered of about 70% in the confront with the corresponding starting value.

EXAMPLE 7

Pharmaceutical formulation, containing the liposomes used in the present invention, for single-dose administration.
3 ml sterile vial containing the lyophilized liposome:

| | |
|---|---|
| phospholipon 90 | mg 100 |
| DIDAB | mg 10 |
| alpha-tocopherol | mg 0.1 |
| saccarose | g 1 |

Before use add 1 ml of water for injection. Add then in a sterile way the following sterile solution, premanufactured in 1 ml disposable sterile syringe is added to the above:

| | |
|---|---|
| polydeoxyribonucleotide (ref. Ex. 1) | mg 10 |
| bihydrate trisodic citrate | mg 2.5 |
| water for injections and preservatives, enough to | ml 1 |

EXAMPLE 8

Extemporaneous pharmaceutical formulation to be used for a whole therapeutic cycle.

30 ml sterile bottle containing the lyophilized liposome:

| | |
|---|---|
| phospholipon 90 | g 1 |
| DIDAB | mg 100 |
| alpha-tocopherol | mg 1 |
| saccarose | g 10 |

Before use add 10 ml of water for injection in a sterile way in the bottle. Add to the so prepared emulsion the following sterile solution contained in a 15 ml bottle or in a 10 ml disposable premanufactured syringe:

| | |
|---|---|
| polydeoxyribonucleotide (ref. Ex. 1) | mg 100 |
| dihydrate trisodic citrate | mg 25 |
| water for injections and preservatives enough to | ml 10 |

The preparation supply a number of 20 mg/die doses for 5 days lasting therapy.

TABLE I

Stability at 30 days of the complex according to Example 1 (group 2 in the Table) in comparison with that of the liposome-polydeoxyribonucleotide complex according to Gursoy et Al. (group 3 in the Table), evaluated by means of the polydeoxyribonucleotide anti-inflammatory activity (reduction of the myeloperoxydase activity in the pleural exudate of rats with pleuritis induced by carragenine)

| group No. | MPO ($\Delta$% vs. CTR) (zero time) | MPO ($\Delta$% vs. CTR) (30 days) |
|---|---|---|
| 2 | −86 | −75 |
| 3 | −85 | −18 |

TABLE II

Stability at 30 days of the complex according to Example 1 (group 3 in the Table) in comparison with that of the liposome-polydeoxyribonucleotide complex according to Gursoy et Al. (group 4 in the Table), evaluated by means of the polydeoxyribonucleotide anti-hypertensive activity.

| group No. | AUC ($\Delta$% vs. CTR) (zero time) | AUC ($\Delta$% vs. CTR) (30 days) |
|---|---|---|
| 2 | 0* | — |
| 3 | −32 | −29 |
| 4 | −30 | −9 |

*The polydeoxyribonucleotide administered dose (10 mg/Kg bolus + 20 mg/Kg/h) is too low to give rise to a meaningful anti-hypertensive activity with respect to the controls.

TABLE III

Stability at 30 days of the complex according to Example 1 (group 3) in comparison with that of the liposome-polydeoxyribonucleotide complex according to Gursoy et Al., (group 4) evaluated through the anti-thrombotic activity of the polydeoxyribonucleotides.

| group No. | AUC (Δ% vs. CTR) (zero time) | AUC (Δ% vs. CTR) (30 days) |
| --- | --- | --- |
| 3 | −85 | −74 |
| 4 | −90 | −24 |

What is claimed is:

1. A pharmaceutical formulation containing complexes of cationic liposomes constituted of phospholipids and polydeoxyribonucleotides having a molecular weight in the range 15,000–50,000, said polydeoxyribonucleotides obtained by depolymerization of nucleic acids, in the complexes the polydeoxyribonucleotides being located on the outer surface of the liposome wherein the weight ratio between the liposome amount and the polydeoxyribonucleotides ranges from 10:2 to 10:0.1.

2. The pharmaceutical formulation according to claim 1 having an anti-inflammatory activity.

3. The pharmaceutical formulation according to claim 1 having an anti-thrombotic activity.

4. The pharmaceutical formulation according to claim 1 having an anti-hypertensive activity.

5. The pharmaceutical formulation according to claim 1 for the therapy of pathologies the treatment of which requires a sustained release of the endothelial prostacyclin.

6. The pharmaceutical formulation according to claim 1 wherein the polydeoxyribonucleotide is defibrotide.

7. The pharmaceutical formulation according to claim 6 wherein the polydeoxyribonucleotide has a molecular weight in the range 15,000–30,000.

8. The pharmaceutical formulation according to claim 1 wherein one or more antioxidants are added.

9. The pharmaceutical formulation according to claim 1, wherein cationic surfactants containing one or more mono-, di-substituted amminic groups, or quaternary ammonium groups, are present, said quaternary ammonium groups containing one or more aliphatic chains with a number of carbon atoms ranging from 8 to 22.

10. The pharmaceutical formulation according to claim 1 wherein the molar ratio between the total amount of the liposome lipid(s) and a cationic surfactant ranges from 10:0.05 to 10:3.

11. The pharmaceutical formulation according to claim 10 wherein the phospholipids in the liposomes include phosphatidylcoline or phosphatidylethanolamine and a second and different lipid and the molar ratio of the phosphatidylcoline or phosphatidylethanolamine: second lipid: cationic surfactant ranges from 9:1:0.05 to 7:3:3.

12. A method for treating inflammation in a patient in need thereof, comprising administering to the patient an antiflammatory effective amount of the pharmaceutical formulation according to claim 1.

13. A method for treating thrombosis in a patient in need thereof, comprising administering to the patient an antiflammatory effective amount of the pharmaceutical formulation according to claim 1.

14. A method for treating hypertension in a patient in need thereof, comprising administering to the patient an antihypertensive effective amount of the pharmaceutical formulation according to claim 1.

15. A method for providing a sustained release of endothelial prostacyclin in a patient in need thereof, comprising administering to the patient a sustained release providing effective amount of the pharmaceutical formulation according to claim 1.

* * * * *